United States Patent
Sagawa et al.

(10) Patent No.: US 6,492,338 B1
(45) Date of Patent: Dec. 10, 2002

(54) THERAPEUTIC AGENTS

(75) Inventors: Hiroaki Sagawa, Kusatsu (JP); Harumi Ueno, Kusatsu (JP); Kaori Akiyama, Kyoto (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/720,308

(22) PCT Filed: Jun. 25, 1999

(86) PCT No.: PCT/JP99/03404
§ 371 (c)(1),
(2), (4) Date: Dec. 26, 2000

(87) PCT Pub. No.: WO00/00190
PCT Pub. Date: Jan. 6, 2000

(30) Foreign Application Priority Data

Jun. 26, 1998 (JP) .......................................... 10-195149

(51) Int. Cl.⁷ ............................................... A61K 31/70
(52) U.S. Cl. ........................ 514/25; 514/23; 549/429; 549/483; 549/484
(58) Field of Search .............................. 514/23, 1.1, 25; 549/429, 483, 484

(56) References Cited

U.S. PATENT DOCUMENTS

| | | | |
|---|---|---|---|
| 4,826,872 A | | 5/1989 | Terao et al. |
| 5,698,585 A | | 12/1997 | Yamakoshi et al. |
| 6,133,238 A | * | 10/2000 | Sagawa et al. |

FOREIGN PATENT DOCUMENTS

| EP | 0 994 111 | 4/2000 |
|---|---|---|

* cited by examiner

Primary Examiner—James O. Wilson
(74) Attorney, Agent, or Firm—Browdy and Neimark, P.L.L.C.

(57) ABSTRACT

Therapeutic or preventive agents for diseases due to the action of aldose reductase; and aldose reductase inhibitors, characterized by containing at least one compound having an aldose reductase inhibiting activity which is selected from among 2,5-dihydroxytetra-hydro-2-furancarboxylic acid, derivatives of the same, optical isomers of both and pharmacologically acceptable salts of them.

4 Claims, No Drawings

THERAPEUTIC AGENTS

This application is a 371 of PCT/JP99/03404, filed Jun. 25, 1999.

TECHNICAL FIELD

The present invention relates to a pharmaceutical composition or a reagent having an aldose reductase inhibitory activity.

BACKGROUND ART

Aldose reductase (hereinafter referred to as AR) is an enzyme involved in a polyol pathway, one of glucose-metabolic pathways, in a living body. The polyol pathway consists of two pathways, i.e., a pathway of reducing glucose to sorbitol involving AR; and a pathway of dehydrogenating sorbitol to D-fructose involving sorbitol dehydrogenase (hereinafter referred to as SDH). It is known that the polyol pathway exists in a number of tissues including brain, liver, pancreas, kidney, adrenal gland, testis, seminal vesicle, placenta, erythrocytes, lens, retina and peripheral nerve. However, the physiological significance of the polyol pathway has been confirmed only in the seminal vesicle, in which it acts as a pathway for producing energy source for sperms. It is believed that, in other sugar-metabolic pathways in normal cells, most of the glucose incorporated into a cell is converted into glucose 6-phosphate by the action of hexokinase to be metabolized in a glycolytic pathway, while only several percents of the glucose is metabolized through the polyol pathway [Tsuyoshi Tanimoto, Pharmacia, 24:459–463 (1988)].

When influx of glucose into a cell increases, the glucose which the glycolytic pathway fails to process is brought to the polyol pathway. The SDH activity is lower than the AR activity. Therefore, an intermediary metabolite, sorbitol, is produced in large quantities if the influx of glucose continues. Sorbitol is highly polar and, therefore, does not efficiently diffuse outside the cell. Thus, sorbitol is accumulated with the cell, resulting in the increase in intracellular osmotic pressure [Tsuyoshi Tanimoto, Pharmacia, 24:459–463 (1988)]. Examples of tissues in which glucose present in blood (blood sugar) unlimitedly flows into cells include insulin-independent tissues such as central nervous system, blood cells and medulla glandulae [Medical Dictionary, 17th edition, Nanzando, Co. Ltd. (1990)].

Diseases due to the accumulation of sorbitol have been reported. For example, diabetic cataract has been reported to be caused as a result of the following steps: AR in lens of eyeballs converts glucose and galactose into corresponding sugar alcohols. The sugar alcohols are inappropriately accumulated in the lens to increase the osmotic pressure. The increased osmotic pressure damages the lens to cause the cataract [see J. H. Kinoshita et al., Biochimica et Biophysica Acta, 158:472 (1968) and references cited therein]. Various harmful influences due to accumulation of sorbitol in lens, peripheral nerve cord and kidney in a diabetic animal have also been reported [see A. Pirie et al., Experimental Eye Research, 3:124 (1964); L. T. Chylack Jr. et al., Investigative Ophthalmology, 8:401 (1969); and J. D. Ward et al., Diabetologia, 6:531 (1970)].

Among complications of diabetes in which blood sugar value is elevated, AR is involved in, for example, cataract, retinopathy, peripheral neuropathy and/or nephropathy. It is essential to inhibit the activity of AR, which is responsible for the above-mentioned complications, as strongly as possible in order to prevent, ameliorate or treat them.

Other diabetic complications include, for example, infectious diseases due to decrease in phagocytosis in leukocytes and diabetic coma [Shin-ban Katei No Igaku, 11th edition, Jiji Press, Ltd. (1996)] and arteriosclerosis due to atheromatous degeneration in great vessel walls [Medical Dictionary, 17th edition, Nanzando, Co. Ltd. (1990)].

OBJECTS OF INVENTION

The main object of the present invention is to develop a compound having an AR inhibitory activity and to provide a pharmaceutical composition for a disease due to AR or a composition for inhibiting AR which contains the compound as its active ingredient.

The other objects and advantages of the present invention will be apparent from the description below.

SUMMARY OF INVENTION

The present inventors demonstrated that 2,5-dihydroxytetrahydro-2-furancarboxylic acid, as well as optical isomers and salts thereof have carcinostatic activities (WO 98/32749). As a result of intensive studies, the present inventors have found that these compounds have highly selective ability of inhibiting an AR activity. Thus, the present invention has been completed.

Thus, the first aspect of the present invention relates to a pharmaceutical composition for treating or preventing a disease due to an AR activity, which contains at least one compound having an AR inhibitory activity selected from the group consisting of 2,5-dihydroxytetrahydro-2-furancarboxylic acid of formula 1:

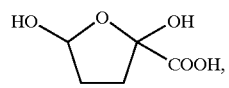

as well as derivatives, optical isomers and pharmacologically acceptable salts thereof.

The second aspect of the present invention relates to a composition for inhibiting AR, which contains at least one compound having an aldose reductase inhibitory activity selected from the group consisting of 2,5-dihydroxytetrahydro-2-furancarboxylic acid, as well as derivatives, optical isomers and salts thereof.

DETAILED DESCRIPTION OF THE INVENTION 2,5-Dihydroxytetrahydro-2-furancarboxylic acid is produced, for example, by heating glucaric acid.

Glucaric acid (also called as saccharic acid) is represented by molecular formula $C_6H_{10}O_8$ (molecular weight 210.14). Glucaric acid is a dicarboxylic acid produced by oxidizing D-glucose, or an oligosaccharide or a polysaccharide that contains D-glucose with nitric acid or the like. It can also be produced by oxidizing D-glucuronic acid with bromine water.

For example, a reaction of glucaric acid at 121° C. for 4 hours results in a reaction mixture containing 2,5-dihydroxytetrahydro-2-furancarboxylic acid. 2,5-Dihydroxytetrahydro-2-furancarboxylic acid can be purified and isolated from the reaction product by subjecting it to reverse phase column chromatography.

2,5-Dihydroxytetrahydro-2-furancarboxylic acid can also be produced by hydrating α-ketoglutarate semialdehyde. α-Ketoglutarate semialdehyde can be produced according to a known method [Journal of Bacteriology, 116:1364–1354 (1973)].

Any derivatives of 2,5-dihydroxytetrahydro-2-furancarboxylic acid may be used in the present invention as long as they have an AR inhibitory activity. Examples of the derivatives include, but are not limited to, a compound of formula 2:

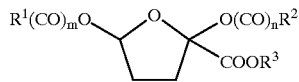

wherein $R^1$, $R^2$ and $R^3$ may be the same or may be different each other, and are hydrogen, an aliphatic group, an aromatic group or an aromatic aliphatic group; m and n are 1 or 0, provided that in case of m=n=0, $R^1$, $R^2$ and $R^3$ are not simultaneously hydrogen.

Examples of aliphatic groups include linear alkyl groups of 1–30 carbons, branched alkyl groups such as isopropyl group, isobutyl group, sec-butyl group, tertbutyl group, isopentyl group, neopentyl group and tertpentyl group, linear alkenyl groups such as etenyl group, allyl group, trans-1-propenyl group, cis-1-propenyl group, cis-8-heptadecenyl group, cis-8-cis-11-heptadecadienyl group, cis-8-cis-11-cis-14-heptadecatrienyl group, cis-5-cis-8-cis-11-heptadecatrienyl group, cis-4-cis-7-cis-10-nonadecatrienyl group, cis-4-cis-7-cis-10-cis-13-nonadecatetraenyl group, cis-4-cis-7-cis-10-cis-13-cis-16-nonadecaheptaenyl group, cis-12-henicosenyl group and cis-3-cis-6-cis-9-cis-12-cis-15-cis-18-henicohexaenyl group, as well as branched alkenyl groups such as isopropenyl group, cis-1-methyl-1-propenyl group, trans-1-methyl-1-propenyl group, trans-1-methyl-1-propenyl group and trans-1-ethyl-1-propenyl group.

Examples of aromatic groups include phenyl group, naphthyl group, biphenyl group, pyrrolyl group, pyridyl group, indolyl group, imidazolyl group, tolyl group, xylyl group, o-chlorophenyl group, o-bromophenyl group, o-nitrophenyl group and o-methoxyphenyl group.

Examples of aromatic aliphatic groups include phenylalkyl groups of 1–15 alkyl group carbons (e.g., benzyl group or phenetyl group), stylyl group and cinnamyl group.

The compound of formula 2 can be produced by reacting 2,5-dihydroxytetrahydro-2-furancarboxylic acid with an alcohol having an aliphatic group, aromatic group or an aromatic aliphatic group and/or a reactive derivative thereof (e.g., alkyl halide, aryl halide, acid ester, diazo compound, salt and alkene produced by dehydrating alcohol), and/or by reacting 2,5-dihydroxytetrahydro-2-furancarboxylic acid with a carboxylic acid having an aliphatic group, aromatic group or an aromatic aliphatic group and/or a reactive derivative thereof (e.g., acid halide, acid anhydride, acid ester and salt).

After the thus produced derivative is purified, its AR inhibitory activity is measured. Then, the derivative can be used in the present invention. The degree of inhibition of alcohol dehydrogenase (hereinafter referred to as ADH) activity by the compound at a concentration that results in 50% inhibition of the AR activity ($IC_{50}$) is 20% or less, preferably 15% or less, most preferably 10% or less.

Furthermore, 2,5-dihydroxytetrahydro-2-furancarboxylic acid or derivatives thereof purified as described above can be optically resolved to obtain 2,5-dihydroxytetrahydro-2-furancarboxylic acid or derivatives thereof in (−) and (+) form.

Optical isomers can be separated by mechanical resolution of racemic mixture, preferential crystallization, resolution by crystallizing as a diastereomeric salt or an inclusion compound, kinetic resolution using an enzyme or a microorganism, chromatographic separation or the like.

Gas chromatography, liquid chromatography, thin-layer chromatography or the like using an appropriate chiral stationary phase can be used for chromatographic resolution.

A method in which a chiral stationary phase is used, a method in which a chiral eluent is used, separation as a diastereomer or the like can be used for optical resolution by liquid chromatography. An amide-type stationary phase, a urea-type stationary phase, a ligand exchange-type stationary phase, a polysaccharide or polysaccharide derivative stationary phase, a protein stationary phase, a polymethacrylate ester stationary phase, a polymethacrylamide stationary phase or the like can be used as a chiral stationary phase. A hexan-type eluent, an alcohol-type eluent, an aqueous (buffer) eluent or the like can be appropriately used as an eluent depending on the stationary phase used.

2,5-dihydroxytetrahydro-2-furancarboxylic acid has two asymmetric carbons at 2-position and 5-position in its molecular structure. Thus, there exist four stereoisomers represented by (2S,5S), (2S,5R), (2R,5S) and (2R,5R) forms. As used herein, 2,5-dihydroxytetrahydro-2-furancarboxylic acid and derivatives thereof include any stereoisomers without being limited to a specific conformation as long as they have an AR inhibitory activity. Furthermore, 2,5-dihydroxytetrahydro-2-furancarboxylic acid and derivatives thereof may be optical isomers or racemic modifications as long as they have an AR inhibitory activity.

2,5-dihydroxytetrahydro-2-furancarboxylic acid has a low activity of inhibiting ADH, which has substrate specificity similar to that of AR. The activities of inhibiting enzymes are highly selective for AR.

Use of esters of pharmaceuticals (e.g., penicillin and non-steroidal anti-inflammatory drug) which are hydrolyzed under physiological conditions as pharmaceuticals has become common. Thus, the active ingredient contained in the pharmaceutical composition for treatment or prevention of the present invention is not specifically limited to the above-mentioned compounds having the AR inhibitory activity. For example, the active ingredient may be a compound that is hydrolyzed under physiological conditions to generate the above-mentioned compound having the AR inhibitory activity. That is, compounds having an AR inhibitory activity as used herein include so-called prodrug compounds, which themselves are inactive, but are converted to compounds having an AR inhibitory activity in vivo.

Examples of esters of 2,5-dihydroxytetrahydro-2-furancarboxylic acid that are hydrolyzed under physiological conditions include a compound of formula 3:

wherein $G_1$ and $G_2$ are independently hydrogen or a group that forms a commonly used ester being able to be hydrolyzed under physiological conditions, provided that $G_1$ and $G_2$ are not simultaneously hydrogen.

The group that forms an ester to be used for $G_1$ can be appropriately selected from, for example, 1H-furan-5-on-1-yl, 1H-isobenzofuran-3-on-1-yl, γ-butyrolacton-4-yl, $—CH_2CH_2NR^4R^5$, $—CHR^6OCOR^7$ or $—CHR^6OCOOR^8$, wherein $R^4$ and $R^5$ are independently (C1–C4) alkyl or $R^4$ and $R^5$ form pyrrolidine, piperidine or morpholine ring together with the nitrogen to which they are attached; $R^6$ is hydrogen or methyl; $R^7$ is (C1–C6) alkyl, (C1–C6) carboxyalkyl, carboxycyclohexyl or carboxyphenyl; and $R^8$ is (C1–C6) alkyl. The group that forms an ester to be used for $G_2$ can be appropriately selected from, for example, acyl group and —PO(ONa)$_2$. Without limitation, acyl groups having a little number of carbons are generally preferable. For example, formyl group, acetyl group and propionyl group are used. The above-mentioned compounds can be prepared from 2,5-dihydroxytetrahydro-2-furancarboxylic acid or optical isomers thereof according to known methods.

Examples of salts used in the present invention include alkaline metal salts, alkaline earth metal salts and salts with organic bases. Pharmacologically acceptable salts mean salts of the above-mentioned compounds having the AR inhibitory activity which are substantially non-toxic to organisms. Examples of pharmacologically acceptable salts include sodium, potassium, calcium, magnesium, ammonium or protonated salts with benzathine(N,N'-dibenzylethylenediamine), choline, ethanolamine, diethanolamine, ethylenediamine, meglumine(N-methylglucamine), benethamine(N-benzylphenetylamine), piperazine or tromethamine(2-amino-2-hydroxymethyl-1,3-propanediol). These salts are obtained by converting a compound having an AR inhibitory activity selected from the group consisting of 2,5-dihydroxytetrahydro-2-furancarboxylic acid, as well as derivatives and optical isomers thereof according to known methods.

The pharmaceutical composition for treating or preventing a disease due to an AR activity, which contains at least one compound having an AR inhibitory activity selected from the group consisting of 2,5-dihydroxytetrahydro-2-furancarboxylic acid, as well as derivatives, optical isomers and pharmacologically acceptable salts thereof as an active ingredient of the first aspect of the present invention may be prepared by formulating at least one compound having an AR inhibitory activity selected from the group consisting of 2,5-dihydroxytetrahydro-2-furancarboxylic acid, as well as derivatives, optical isomers and pharmacologically acceptable salts thereof as an active ingredient with a known pharmaceutical carrier.

At least one compound having an AR inhibitory activity selected from the group consisting of 2,5-dihydroxytetrahydro-2-furancarboxylic acid, as well as derivatives, optical isomers and pharmacologically acceptable salts thereof is generally mixed with a pharmaceutically acceptable liquid or solid carrier and, optionally, solvent, dispersing agent, emulsifier, buffering agent, stabilizer, excipient, binder, disintegrant, lubricant and the like to formulate it. The formulation may be in a form of a solid preparation such as tablet, granule, powder, epipastic and capsule, or a liquid preparation such as normal solution, suspension and emulsion. In addition, the composition may be formulated into a dried preparation, which can be reconstituted as a liquid preparation by adding an appropriate carrier before use.

The pharmaceutical carrier can be selected according to the above-mentioned particular administration route and dosage form. For an oral preparation, starch, lactose, sucrose, mannit, carboxymethylcellulose, cornstarch, inorganic salts and the like are utilized, for example. Binder, disintegrant, surfactant, lubricant, fluidity-promoting agent, tasting agent, coloring agent, flavoring agent and the like can also be included in oral preparations.

A parenteral preparation can be prepared according to conventional methods by dissolving or suspending at least one compound having an AR inhibitory activity selected from the group consisting of 2,5-dihydroxytetrahydro-2-furancarboxylic acid, as well as derivatives, optical isomers and pharmacologically acceptable salts thereof, in a diluent. The diluents include injectable distilled water, physiological saline, aqueous glucose solution, injectable vegetable oil, sesame oil, peanut oil, soybean oil, corn oil, propylene glycol and polyethylene glycol. Optionally, sterilizer, stabilizer, osmotic regulator, smoothing agent and the like may be added to the solution or suspension.

The pharmaceutical composition for treating or preventing a disease due to an AR activity of the present invention (hereinafter simply referred to as the pharmaceutical composition of the present invention) is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the pharmaceutical composition of the present invention is appropriately determined and varies depending on the particular dosage form, administration route and purpose as well as age, weight and conditions of a patient to be treated. In general, a daily dosage for an adult person is 0.1 to 2000 mg/kg in terms of the amount of at least one compound having an AR inhibitory activity selected from the group consisting of 2,5-dihydroxytetrahydro-2-furancarboxylic acid, as well as derivatives, optical isomers and pharmacologically acceptable salts thereof contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

Since the pharmaceutical composition of the present invention has an AR inhibitory activity, it can be used for preventing and/or treating a disease due to an AR activity. Examples of the diseases due to an AR activity include diabetic complications as described above. Specifically, such diseases include cataract, peripheral neuropathy, retinopathy and/or nephropathy. The pharmaceutical composition of the present invention can be used in order to prevent and/or treat such diseases.

A dosage of the pharmaceutical composition for preventing and/or treating diabetic complications including cataract, peripheral neuropathy, retinopathy and/or nephropathy is appropriately determined and varies depending on the particular dosage form, administration route and purpose as well as age, weight and conditions of a patient to be treated. In general, a daily dosage for an adult person is 1 to 1000 mg, preferably 10 to 200 mg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The pharmaceutical composition of the present invention may be used in combination with a substance having an AR inhibitory activity derived from plants. Any plants may be used as long as they contain a substance having an AR inhibitory activity. Examples of the plants include, but are not limited to, those belonging to family Liliaceae. Examples of the plants belonging to family Liliaceae include onions (Allium cepa) belonging to genus Allium. A substance having an AR inhibitory activity can be prepared from onions, for example, by extracting bulbs or bulb pellicles of onions with hot water. The extract having an AR inhibitory activity may be used in combination with the pharmaceutical composition of the present invention. The onion extract having an AR inhibitory activity may be used alone.

The process for preparing a substance having an AR inhibitory activity from bulbs or bulb pellicles of onions is not limited to a specific one. For example, after bulb pellicles of onions are washed with water, water is added thereto to adjust the content of pellicles to 0.1 to 20% by weight. The mixture is heated at 50 to 130° C. for several minutes to several hours. Thus, an extract containing a substance having an AR inhibitory activity at a high concentration can be obtained. The extract selectively inhibits AR. Therefore, the extract is used for a healthy drink useful for treating or preventing a disease due to an AR activity. Such a healthy drink may be produced by using an extract of bulbs and/or bulb pellicles of onions as an active ingredient according to a conventional method for producing drinks. Alternatively, flavonoid compounds having an AR inhibitory activity such as spiraein, quercetin, quercitrin and myricetin may be concentrated from the extract for use as active ingredients. In addition, the flavonoid compounds may be used in combination with the pharmaceutical composition of the present invention.

No toxicity is observed when a physiologically effective amount of a compound having an AR inhibitory activity selected from the group consisting of 2,5-dihydroxytetrahydro-2-furancarboxylic acid, as well as derivatives, optical isomers and pharmacologically acceptable salts thereof used in the present invention was orally administered to a mouse.

The composition for inhibiting AR of the second aspect of the present invention may be prepared by formulating at least one compound having an AR inhibitory activity selected from the group consisting of 2,5-dihydroxytetrahydro-2-furancarboxylic acid, as well as derivatives, optical isomers and salts thereof into a conventional reagent form according to the method as described above with respect to the production of the pharmaceutical composition. The inhibitory composition is useful for studying diseases involving AR and for screening AR inhibitors.

The following Examples further illustrate the present invention in detail but are not to be construed to limit the scope thereof. Percent (%) in Examples means percent by weight unless otherwise stated.

EXAMPLE 1

(1) D-saccharate 1,4-lactone-hydrate (Nacalai Tesque, 304–35) was dissolved in 100 ml of water. The pH of the solution was 2.5. 30 ml of the resulting solution was then heated at 121° C. for 4 hours.

The heated solution was subjected to HPLC under the following conditions. 2,5-dihydroxytetrahydro-2-furancarboxylic acid eluted in fractions at 13.5 to 15 minutes was collected in large quantities, and concentrated to dryness under reduced pressure.

Column: TSKgel ODS-80Ts (5 µm), 20 mm×25 cm;
Mobile Phase A: 0.1% aqueous trifluoroacetic acid solution;
Mobile Phase B: aqueous solution containing 0.1% trifluoroacetic acid/50% acetonitrile;
Flow rate: 8 ml/minute;
Elution: 100% Mobile Phase A (10 minutes)→from 100% Mobile Phase A to 100% Mobile Phase B (40 minutes);
Detection: absorbance at 215 nm.

(2) Confirmation of AR inhibitory activity of 2,5-dihydroxytetrahydro-2-furancarboxylic acid.

2,5-dihydroxytetrahydro-2-furancarboxylic acid was added to an AR reaction system to determine the AR inhibitory activity.

NADPH (Nacalai Tesque) as a hydrogen donor and methylglyoxal (Nacalai Tesque) as a substrate for the enzyme were used. A commercially available enzyme solution (Wako Pure Chemical Industries, code 012-13991) was diluted. for use as AR.

The AR activity was measured as follows.

40 µl of sterile pure water, 20 µl of 1 mM aqueous NADPH solution and 10 µl of enzyme dilution were added to 100 µl of 200 mM phosphate buffer (pH 6.2). 10 µl of sterile pure water was further added to the mixture. After 20 µl of 100 mM aqueous methylglyoxal solution was added thereto, the change in absorbance at 340 nm was monitored at room temperature for 3 minutes. The enzymatic activity was determined on the basis of the change in absorbance per minute. Next, aqueous solution of 2,5-dihydroxytetrahydro-2-furancarboxylic acid at a varying concentration was added to the reaction system as described above in place of 10 µl of sterile pure water. The enzymatic activity was then determined as described above.

The AR inhibitory activity of 2,5-dihydroxytetrahydro-2-furancarboxylic acid was determined based on the enzymatic activity inhibition rate calculated according to the following equation:

Enzymatic activity inhibition rate (%)={1-(enzymatic activity with the addition of aqueous 2,5-dihydroxytetrahydro-2-furancarboxylic acid solution)/(enzymatic activity with the addition of water)}×100.

If 2,5-dihydroxytetrahydro-2-furancarboxylic acid does not have an AR inhibitory activity, the enzymatic activity inhibition rate is 0%.

The activity inhibition rate on the AR activity of 2,5-dihydroxytetrahydro-2-furancarboxylic acid is shown in Table 1.

TABLE 1

| Concentration in enzymatic reaction system (µg/ml) | Activity inhibition rate (%) |
|---|---|
| 0.5 | 8.1 |
| 5 | 34.8 |
| 50 | 81.6 |
| 500 | 96.3 |

The concentration in enzymatic reaction system in Table 1 means the concentration of 2,5-dihydroxytetrahydro-2-furancarboxylic acid in the enzymatic reaction system as described above. The concentration of 2,5-dihydroxytetrahydro-2-furancarboxylic acid in the enzymatic reaction mixture that results in the activity inhibition rate of 50% ($IC_{50}$) as calculated based on the concentration in enzymatic reaction system and the AR activity inhibition rate was about 10.8 µg/ml.

Next, 2,5-dihydroxytetrahydro-2-furancarboxylic acid was added to an ADH reaction system to determine the ADH inhibitory activity.

A commercially available lyophilized product (Nacalai Tesque, code 012-83) was dissolved in water for use as ADH. NAD (Nacalai Tesque) as a hydrogen donor and ethanol (Nacalai Tesque) as a substrate for the enzyme were used.

The ADH activity was measured as follows.

50 µl of water, 20 µl of 3 mM aqueous NAD solution and 10 µl of enzyme solution were added to 100 µl of 200 mM phosphate buffer (pH 6.2). 10 μl of sterile pure water was further added to the mixture. After 10 μl of 60% ethanol was added thereto, the change in absorbance at 340 nm was monitored at room temperature for 3 minutes. The enzymatic activity was determined on the basis of the change in absorbance per minute.

Next, aqueous solution of 2,5-dihydroxytetrahydro-2-furancarboxylic acid at a final concentration of 10.8 μg/ml and sterile pure water were added to the reaction system as described above in place of 10 μl of sterile pure water. The enzymatic activity was then determined as described above. The ADH enzymatic activity inhibition rate was calculated according to the above-mentioned equation based on the enzymatic activity.

The ADH activity inhibition rate of 2,5-dihydroxytetrahydro-2-furancarboxylic acid at $IC_5$ for AR activity was 7.1%, indicating that the AR inhibitory activity of the compound is highly selective.

In addition, other derivatives had equivalent activities.

EXAMPLE 2

Injectable Preparation (1) 0.1% solution of 2,5-dihydroxytetrahydro-2-furancarboxylic acid in injectable distilled water was prepared and sterilized by filtration to prepare an injectable preparation.

(2) 1% solution of 2,5-dihydroxytetrahydro-2-furancarboxylic acid in injectable distilled water was prepared. An aliquot of the solution corresponding to 10 mg of dry material was dispensed into a vial for lyophilization, and then lyophilized. 2 ml of saline was separately attached thereto for dissolution.

EXAMPLE 3

Tablet

Tables were formulated as follows.

| | |
|---|---|
| 2,5-Dihydroxytetrahydro-2-furancarboxylic acid | 10 mg |
| Cornstarch | 65 mg |
| Carboxymethylcellulose | 20 mg |
| Polyvinylpyrrolidone | 3 mg |
| Magnesium stearate | 2 mg |
| Total weight in a tablet | 100 mg |

As described above, the present invention provides a pharmaceutical composition effective for preventing and/or treating a disease due to AR activity such as diabetic complications including cataract, peripheral neuropathy, retinopathy and nephropathy, which has a highly selective physiological AR inhibitory activity and which is highly safe for a living body, or a composition for inhibiting AR.

What is claimed is:

1. A method for treating a disease due to an aldose reductase activity or a disease complication of said disease, which comprises administering at least one compound having an aldose reductase inhibitory activity selected from the group consisting of 2,5-dihydroxytetrahydro-2-furancarboxylic acid of formula 1:

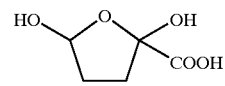

as well as derivatives, optical isomers and pharmacologically acceptable salts thereof, wherein said derivatives are selected from the group consisting of compounds of formula 2:

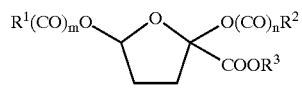

wherein $R^1$, $R^2$ and $R^3$ may be the same of may be different from each other, and are hydrogen, an aliphatic group, an aromatic group or an aromatic aliphatic group; m and n are 1 or 0, provided that in case of m=n=0, $R^1$, $R^2$ and $R^3$ are not simultaneously hydrogen.

2. The method according to claim 1, wherein said disease complication is a diabetic complication due to the aldose reductase activity.

3. The method according to claim 1, wherein the diabetic complication is cataract, peripheral neuropathy, retinopathy and/or nephropathy due to the aldose reductase activity.

4. A method for inhibiting aldose reductase, which comprises inhibiting aldose reductase using at least one compound having an aldose reductase inhibitory activity selected from the group consisting of 2,5-dihydroxytetrahydro-2-furancarboxylic acid of formula 1:

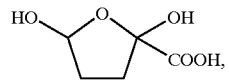

as well as derivatives, optical isomers and salts thereof, wherein said derivatives are selected from the group consisting of compounds of formula 2:

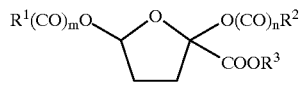

wherein $R^1$, $R^2$ and $R^3$ may be the same or may be different each other, and are hydrogen, an aliphatic group, an aromatic group or an aromatic aliphatic group; m and n are 1 or 0, provided that in case of m=n=0, $R^1$, $R^2$ and $R^3$ are not simultaneously hydrogen.

* * * * *